United States Patent [19]

Patrick et al.

[11] Patent Number: 4,810,493

[45] Date of Patent: Mar. 7, 1989

[54] METHOD FOR THE CULTURE OF THE TRT/SHS VIRUS, AND VACCINE THEREFROM, ESPECIALLY FOR THE TREATMENT OF TURKEYS

[75] Inventors: Giraud Patrick; Benne jean Georges; Guittet Michéle, all of Saint-Brieuc; Toquin Didier, Quintin, all of France

[73] Assignees: Rhone-Merieux, Lyons; Ministere de l'Agriculture Direction de la Qualite Services Veterinaires Laboratoire National de Pathologie Aviaire, Ploufragan, both of France

[21] Appl. No.: 86,358

[22] Filed: Aug. 17, 1987

[30] Foreign Application Priority Data

Aug. 18, 1986 [FR] France .................................. 86 11872

[51] Int. Cl.$^4$ .......................... A61K 39/12; C12N 7/00
[52] U.S. Cl. ...................................... 424/89; 435/235; 435/236; 435/237
[58] Field of Search ....................... 435/235, 236, 237; 424/89

[56] References Cited

U.S. PATENT DOCUMENTS 4,505,892  3/1985  Apontoweil et al. ............... 435/235
4,692,410  9/1987  Apontoweil et al. ............... 435/235

*Primary Examiner*—Sam Rosen
*Attorney, Agent, or Firm*—Roland Plottel

[57] ABSTRACT

The invention concerns a method for the culture of the infectious rhinotracheitis virus, TRT/SHS in the turkey that is also responsible for disorders in other bird species such as the infectious big head syndrome (or swollen head syndrome) in the chicken and guinea fowl.

According to the invention, samples are taken from sick animals that are inoculated on cell cultures consisting of a continuous line of monkey kidney cells.

A large quantity of the virus is obtained. This can be used as an antigen in the production of a vaccine that can be equally used for the immunization of all bird species.

The invention also applies to the production of vaccines from viral strains obtained by means of this method.

9 Claims, No Drawings

METHOD FOR THE CULTURE OF THE TRT/SHS VIRUS, AND VACCINE THEREFROM, ESPECIALLY FOR THE TREATMENT OF TURKEYS

The invention concerns a culture method for the virus provoking infectious rhinotracheitis in the turkey. This virus is also responsible for disorders in other species of birds such as the infectious big head syndrome (or swollen head syndrome) in the chicken or guinea fowl. This virus will be called the TRT/SHS virus in the rest of the description. The invention also concerns any vaccine prepared from the virus obtained by this method. These disorders result in economic losses due to poor performance, death and seizures in the slaughterhouse. These contagious diseases spread quickly among all of the animals in the same building and from one farm to another.

The development of a method for the prevention of these diseases is absolutely necessary.

The TRT/SHS virus was isolated by the applicants in young turkeys striken with infectious rhinotracheitis and in chickens and guinea fowl striken with the infectious big head syndrome. The virus has been described by GIRAUD Patrick, BENNEJEAN Georges, GUITTET Michèle and TOQUIN Didier in "Semaine Vétérinaire" (1986, 413, 1–3).

This viral agent was first found in samples of sick or autopsied animals, by culture on trachea rings from turkey embryos specific pathogen free (SPF), or chicken embryos (SPF), in which the virus induces a stop in ciliary movements within 5 to 8 days.

Observation by electron microscope of this viral agent was possible after ultracentrifugation of the trachea ring culture medium. The virus appears as enveloped particles and covered with spikes. The morphology of this virus will be described in greater detail below.

All of the characteristics of this virus indicate that it is a pseudomyxovirus and more generally, that it belongs to the family of Paramyxoviridae.

The applicants observed that after infection by the TRT/SHS virus and cure, the birds became resistant to further infection. This means that the birds have an immunitary response of excellent quality towards infection by the virus and can therefore be protected from the disease by vaccination. However, in order to create such a vaccine in optimum conditions, the conditions for the cultivation of this virus have to be compatible with the laws of the market. Of course, already familiar methods for virus culture have been tried: for example, culture on trachea rings of chicken or turkey embryos or culture on chicken or turkey embryo eggs. Unfortunately, the effectiveness of such cultures as applied to the TRT/SHS virus has been found to be too small for the production of a vaccine to be possibility in acceptable profit-earning conditions.

The purpose of the present invention is to overcome these disadvantages and concerns a new method for TRT/SHS virus culture that leads to considerable multiplication of the virus. It also concerns any vaccine obtained from the TRT/SHS virus thereby obtained.

The present invention more specifically concerns a method for TRT/SHS virus culture that is characterized in that the culture substrate consists of a continuous line of monkey kidney cells.

The present invention will be better understood with the help of the following explanations and examples.

According to an important characteristic of the invention and in accordance with an experiment carried out by the applicants, the culture of the TRT/SHS virus is carried out on continuous lines of monkey kidney cells, in particular, African Green (Vero, BSC-1), Rhesus (LLC-MK2, MA 104) and Buffalo Green (BGM) monkey kidney cells.

According to the invention, the method consists of inoculating cell cultures of these continuous lines of monkey kidney cells, incubating the cultures in the presence of the TRT/SHS virus and collecting the virus after multiplication in these cells.

The main stages in the method will be described with more precision below. A method in accordance with the invention enables the production of a large quantity of virus that can be used as antigen in the preparation of a vaccine against disorders due to the TRT/SHS virus in all species of birds, and a reagent for a serology technique to reveal antibodies directed against the virus.

According to an important characteristic of the invention, the viral strains obtained by the method previously described for the culture of the TRT/SHS virus on monkey kidney cells are used in the production of vaccines according to the methods described below by way of non-limitative example.

In order to produce a vaccine, the virus used is deprived of its pathological power, without it losing its antigenic activity, that is, its ability to stimulate the production of antibodies or even to induce an immunoresponse. In order to do so, the virus can be attenuated or inactivated.

In order to prepare an attenuated living virus vaccine against disorders due to the TRT/SHS virus described above, the virus is put through the minimum number of passages necessary for this attenuation, for example, more than 10 and up to 200, on monkey kidney cells, according to the method described above. After verification of the attenuation of the pathological power of the virus by inoculation on the sensitive animal, for example, the young turkey (SPF) or chicken (EOPS), the vaccine can be produced on monkey kidney cells according to the method complying with the previously described invention.

In order to prepare a vaccine with an inactivated virus against diseases due to the TRT/SHS virus in all species of birds, it is necessary to cultivate the virus as described above on monkey kidney cells, in order to obtain a higher titer. Moreover, it is possible to select a viral clone that is appropriate for the production requirements. The virus is then inactivated according to the standard methods for the inactivation of virus described below.

An important characteristic of the vaccine according to the invention is that it can be used indifferently for the immunization of all species of bird, independent of the species of bird that is the source of the virus used for the preparation of the vaccine.

Before developing the applications for the culture method and multiplication of the TRT/SHS virus described above, it is necessary to characterize this virus:

1. The virus comprises a nucleic acid of the RNA type. The multiplication of the virus in monkey kidney cells is not significantly affected by the addition of IUdR (5-iodo-uracil-2'-desoxyriboside) in the culture medium.

2. The virus is sensitive to the action of solvents of lipids. Treatment of the supernatant of the monkey kidney cell cultures infected by the virus with ether of chloroform induces a significant reduction in the infectious titer. This is a characteristic of enveloped virus that contain lipids.

3. Examination by electron microscope of the viral preparation derived from the supernatant of monkey kidney cell cultures infected by the virus reveals very polymorphous coated particles surrounded with spikes. The virus comprises a central nucleocapsid arranged in a ball. The virus has very variable dimensions. The average diameter varies from 100 to 200 nanometers with extremes going from about 70 to 600 nanometers. Circular, oval, filamentous or very variable forms are observed. The spikes are about 12 to 15 nanometers long. The nucleocapsid appears as a spiral structure about 15 nanometers in diameter.

Electron microscope examination of ultra-thin sections of the monkey kidney cells infected with the virus reveal the budding of virions at the outer cell membrane locally thickened by the accumulation of viral matter. An accumulation of viral matter is also observed in the intracytoplasmic inclusions.

4. There are many serum tests for antibodies directed against the TRT/SHS virus. We can mention: seroneutralization on monkey kidney cell culture or other culture substrate, immunofluorescence on infected monkey kidney cell cultures and the serology method known as E.L.I.S.A. with an antigen produced on monkey kidney cells. These different techniques do not reveal any common antigens between the TRT/SHS virus and other bird virus or morphologically close mammal virus.

5. The virus does not have the characteristic of spontaneous hemagglutination (chicken, turkey, horse, cattle, duck, sheep, guinea-pig, pig and human red blood cells). The virus also does not have any detectable neuraminidasic activity.

6. Experimental intra-nasal inoculation of the non-attenuated pathological virus on monkey kidney cells enables reproduction of characteristic infectious rhinotracheitis on young turkeys (SPF) and enables reproduction of the preliminary symptoms of the SIGT in the chicken and guinea fowl. The characteristic histological lesions corresponding to eosinophilic intracytoplasmic inclusions are observed in the ciliated cells of the epithelium of the upper respiratory passages (trachea, larynx, nasal cavities).

The characteristics of the virus therefore indicate, as mentioned above, that it belongs to the group of pseudomyxovirus and more generally, to the family of Paramyxoviridae.

The method described above concerning the culture, multiplication and attenuation of the TRT/SHS virus thereby characterized, in particular leading to the obtention of the vaccine, is now illustrated by means of the following non-limiting examples.

EXAMPLE I

Isolation, culture and multiplication of the TRT/SHS virus on monkey kidney cells Samples are taken from sick animals (tracheal swabs, suction of nasal mucus, etc.) or autopsied animals (crushing of respiratory tract organs, especially the upper passages, etc.) The samples, kept at a low temperature (for example +4° C.) are suspended in a transfer medium containing antibiotics (the medium can be peptonated water, "phosphate" buffer, etc.) The suspensions are filtered.

The filtrates are then inoculated on continuous lines of monkey kidney cells. In particular, cells commonly called "VERO" are used. They are derived from the African Green monkey kidney. These cells are marketed by the FLOW Laboratories under the number ATCC:CCL.81 and kept beyond the 130th passage.

10 ml of a cell suspension with a concentration of 250,000 VERO cells per milliliter is prepared for a 25 $cm^2$ dish. 100 microliters of sample are inoculated per dish, preferably on a still unestablished cell layer. Eagle's essential minimum medium can be used with Earle's salts, diluted with Hépès buffer, foetal calf serum and antibodies. It is incubated at 37° C. The presence of the virus is observed several days later by the appearance of a cytopathic effect. According to a first variant, a subculture of the infected layer is made after several days. According to a second variant, a co-culture is made of infected cells and healthy cells. In both cases, a greater cytopathic effect is obtained within several days.

The cytopathic effect (lesions of the cell layer) results in distended, rounded, refractive cells that detach and float on the culture supernatant. After several methods of coloration (May-Gründwald-Giemsa, etc.), the appearance of one or several voluminous intracytoplasmic inclusions is found that slightly push aside the nucleus. The viral inclusion appears to be eosinophilic with hematoxylin-eosin staining.

The nucleus does not present an inclusion although there is sometimes a margination of the chromatin that is clearly visible with acridine orange staining. The virus also induces the appearance of syncytia.

The virus is revealed in the culture supernatant by electron microscopy. The virus is then collected and stored at $-70°$ C.

Once the isolation has been carried out as described above, the viral strain can then be adapted by several successive passages on the chosen substrate, for example VERO cells. Once well adapted, the strain induces a well visible cytopathic effect within several days. This culture method on monkey kidney cells, in particular on VERO cells, ensures satisfactory multiplication of the TRT/SHS virus.

EXAMPLE II

Preparation of an attenuated living virus from the TRT/SHS virus

It is necessary to proceed with the attenuation of the TRT/SHS virus in order to prepare an attenuated living vaccine. Isolation and multiplication are carried out as in example I. In order to attenuate the viral strain, a great many passages are carried out on the culture substrate formed in accordance with the invention by monkey kidney cells. For example, the number of passages can vary from 10 to 200. Attenuation of the pathogenic power of the virus can be verified by inoculation in a sensitive animal, for example the young turkey (SPF) and chichen (SPF).

After multiplying the attenuated viral strain on monkey kidney cells, the culture surface layer and/or the cells are collected. The collected cells can be put through an ultrasound treatment. The viral suspension is stored at a low temperature (at least $-20°$ C. but preferably $-70°$ C.). It is possible to add a stabilizing agent such as carbohydrates (sorbitol, mannitol, starch, sucrose, dextran, glucose, etc.), proteins (albumins, casein, etc.), an agent containing proteins (bovin serum, skin milk, etc.) and buffer (alkaline metal phosphate etc.). The mixture described by Bovarnick under the name of SPGA can be used as a stabilizing agent (Journal Bact. 1950, 59, 509).

The preparation can be lyophilized after adding a stabilizer and it can be vacuum or nitrogen stored. An additive such as aluminium hydroxide can be added.

EXAMPLE III

Preparation of an inactivated vaccine from the TRT/SHS virus

Proceed as follows if the virus is intended for the preparation of an inactivated vaccine. After carrying out the isolation and multiplication according to example I, the viral preparation is titered. Inactivation is carried out by formaldehyde (at the final concentration of 0.2 to 0.4% for 24 hours at 20° C. or 2 hours at 37° C.), organic solvents (halogenated carbohydrates in the presence of a surface-active agent such as a monooleate of polyoxyethelene sorbitane), beta-propiolactone, ethylene-imine or their derivatives. It is also possible to inactivate the virus by cleavage according to different methods, for example for use of an enzyme and/or an organic solvent.

After inactivation, the inactivation agent can be neutralized (for example, formaldehyde by thio-sulphate). The pH is then adjusted to 7. A sample is tested in order to verify the inactivation, mainly by testing for the absence of cytopathic effect on monkey kidney cell cultures. It is stored at a low temperature (for example, −20° C.). Finally, the inactivated virus is mixed with an additive, for example, aluminium hydroxide or a composition formed from a mineral oil and one or several emulsifiers.

The viral suspension is emulsified in the oily phase of the additive.

EXAMPLE IV

Administration of vaccines prepared from the TRT/SHS virus

The vaccine is administered to bird species sensitive to the disease. Vaccination can take place from the age of 1 day right until the beginning of the laying period and booster shots can be administered. The attenuated vaccine is administered by spraying, addition to the drinking water, deposit of a small drop in the eye or nasal openings, tracheal or cloacal swabbing or injection. The inactivated vaccine should be administered by injection, for example, subcutaneous or intramuscular injection.

Since the previously described methods concern the culture, multiplication, attenuation of the TRT/SHS virus, the antigen preparation for the vaccination and the serology, the invention applies to the detection and prevention of infectious rhinotracheitis in the turkey, the infectious big head syndrome in the chicken and guinea fowl and disorders due to the TRT/SHS virus in other bird species such as coryza in the guinea fowl and respiratory diseases in the duck, goose, pheasant, quail, etc.

It is advisable to note that a previously described strain of the infectious rhinotracheitis virus in the turkey was registered at the Collection Nationale de Cultures de Miroorganismes de l'Institut Pasteur, 25 rue du Docteur Roux, 75724 PARIS Cedex 15 under the following references:

Viral strain 86004
Batch (OVS 5)
registered on Oct. 9, 1986
under N° I 611

We claim:

1. A method for the culture of the TRT/SHS virus, characterized in that said virus is cultured on a culture substrate, formed from a continuous monkey kidney cell line.

2. A culture method according to claim 1, characterized in that the virus is multiplied by several passages on such substrate.

3. A culture method according to claim 1, characterized in that the virus is cultured through many passages on the substrate until attenuated.

4. A vaccine intended for the immunization of bird species against the TRT/SHS virus, characterized in that it is prepared by attenuation or inactivation of the viral strain obtained by the method according to claim 1.

5. A lving virus vaccine according to claim 4, characterized in that the strain is attenuated by a great number of passages on said substrate.

6. An inactivated virus vaccine according to claim 4, characterized in that the strain is prepared by inactivation.

7. A method for the immunization of bird species, characterized in that such species are treated with sufficient vaccine according to claim 4 to cause immunization against the TRT/SHS virus.

8. A method according to claim 7, characterized in that the bird species immunized is the same as the bird species from which the virus used for preparation of the vaccine was obtained.

9. A method according to claim 7, characterized in that the bird species immunized is different from the bird species from which the virus used for preparation of the vaccine was obtained.

* * * * *

UNITED STATES PATENT AND TRADEMARK OFFICE
CERTIFICATE OF CORRECTION

PATENT NO. : 4,810,493
DATED : March 7, 1989
INVENTOR(S) : Patrick Giraud, Georges Bennejean, Michele Guittet, Didier Toqui It is certified that error appears in the above-identified patent and that said Letters Patent is hereby corrected as shown below:

On the title page:

line 2, change "Patrick et al." to -- Giraud et al. --;

left column, after "[75] Inventors:", change "Giraud Patrick" to -- Patrick Giraud --; change "Benne jean Georges" to -- George Bennejean --; change "Guittet Michéle" to -- Michéle Guittet --; change "Toquin Didier" to -- Didier Toquin --;

UNITED STATES PATENT AND TRADEMARK OFFICE
CERTIFICATE OF CORRECTION

PATENT NO. : 4,810,493

DATED : March 7, 1989

INVENTOR(S) : Patrick Giraud, et al

Page 2 of 2

It is certified that error appears in the above-identified patent and that said Letters Patent is hereby corrected as shown below:

left column, after "[73] assignees;", after Rhone-Meriex", change"Lyons" to --Lyon--.

Signed and Sealed this

Seventeenth Day of July, 1990

Attest:

Attesting Officer

HARRY F. MANBECK, JR.

Commissioner of Patents and Trademarks